(12) United States Patent
Kaeppler et al.

(10) Patent No.: US 11,998,007 B2
(45) Date of Patent: Jun. 4, 2024

(54) MAIZE POLLEN COMPOSITION FOR COLLECTING POLLEN AND STORING POLLEN

(71) Applicant: WISCONSIN ALUMNI RESEARCH FOUNDATION, Madison, WI (US)

(72) Inventors: Shawn Kaeppler, Middleton, WI (US); Heidi Kaeppler, Middleton, WI (US); Michael William Petersen, Merrimac, WI (US); Brian Joseph Martinell, Mount Horeb, WI (US); Frank McFarland, Middleton, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 17/694,200

(22) Filed: Mar. 14, 2022

(65) Prior Publication Data

US 2022/0287299 A1 Sep. 15, 2022

Related U.S. Application Data

(60) Provisional application No. 63/160,427, filed on Mar. 12, 2021.

(51) Int. Cl.
*A01N 3/00* (2006.01)
*A01H 5/10* (2018.01)
*A01H 6/46* (2018.01)

(52) U.S. Cl.
CPC .............. *A01N 3/00* (2013.01); *A01H 5/10* (2013.01); *A01H 6/4684* (2018.05)

(58) Field of Classification Search
CPC ........ A01H 6/4684; A01H 6/28; A01H 6/384; A01H 5/10; A01N 3/00
See application file for complete search history.

(56) References Cited

U.S. PATENT DOCUMENTS

| | | | |
|---|---|---|---|
| 5,689,914 A | 9/1997 | Greaves et al. | |
| 6,141,904 A | 11/2000 | Greaves et al. | |
| 6,146,884 A | 11/2000 | Coonrod et al. | |
| 10,575,517 B2 | 3/2020 | Cope et al. | |
| 2019/0008144 A1* | 1/2019 | Etter | ........................ A01H 1/00 |
| 2020/0296954 A1 | 9/2020 | Cope et al. | |

OTHER PUBLICATIONS

Gaudet et al. Development and Optimization of a Germination Assay and Long-term Storage for Cannabis sativa Pollen, Plants 2020, 9 665, 1-10. (Year: 2020).*
Gilbert et al. Description of Particle size, Distribution, and Behavior of Talc Preparations Commercially Available Within the United States, J Bronchol Intervent Pulmonol, vol. 25, No. 1 2018, 25-30. (Year: 2018).*
Salomon-Torres et al. Date Palm Pollen: Features, Production, Extraction and Pollination Methods, Agronomy Mar. 8, 2021, 11, 504, 1-21. (Year: 2021).*
SSP Seals blog 2018, retrieved on Jan. 23, 2023 at https://www.sspseals.com/blog/properties-benefits-peek-material, 3 pp. (Year: 2018).*
US EPA Commodity Inert Ingredients, retrieved on Jan. 23, 2023 at at https://www.epa.gov/pesticide-registration/commodity-inert-ingredients, 11 pp. (Year: 2023).*
Yi et al. Polyester and nylon powders used as pollen diluents preserve pollen germination and tube growth in controlled pollinations, Sex Plant Reprod (2003) 15:265-269. (Year: 2003).*
Hofmann, F., Otto, M. & Wosniok, W., "Maize pollen deposition in relation to distance from the nearest pollen source under common cultivation—results of 10 years of monitoring (2001 to 2010)." Environ Sci Eur 26, 24 (2014). https://doi.org/10.1186/s12302-014-0024-3.
Jaeger, H. M., & Nagel, S. R. (1992). Physics of the Granular State. Science 255(5051), 1523-1531.
Pareddy et al., Production of normal, geminable and viable pollen from in vitro-cultured maize tassels, (1989) Theor Appl Genet 77:521-526.

* cited by examiner

*Primary Examiner* — June Hwu
(74) *Attorney, Agent, or Firm* — Quarles & Brady, LLP

(57) ABSTRACT

A maize pollen composition containing polyether ether ketone and pollen for collecting pollen and storing pollen.

4 Claims, 12 Drawing Sheets
(11 of 12 Drawing Sheet(s) Filed in Color)

Figure 2

| Test | # Fail | # Success (at least ~10 kernels) | Genotype |
|---|---|---|---|
| 7/24 1:5 dilution Shawn's puffer | 4 | | MBS5411 |
| 7/24 1:5 dilution shaker | 1 | 5 | MBS5411 |
| 7/24 1:5 dilution Harris blaster | 1 | 5 | MBS5411 |
| 7/24 1:10 dilution with shaker | | 4 | MBS5411 |
| Day 2, 1:10 dilution | | 5 | MBS5411 |
| Day 2, 1:5 dilution | | 5 | MBS5411 |
| Day 2, 1:10+2 hours | 3 | | MBS5411 |
| Day 3, 1:10 dilution | 2 | 3 | MBS5411 |
| Day 3, 1:5 dilution | | 5 | MBS5411 |
| Day 3, 1:10 dilution+2 hours | 3 | | MBS5411 |
| Day 4, 1:5 dilution | | 5 | MBS5411 |
| Day 4, 1:10 dilution +2 hours | 3 | | MBS5411 |
| Day 4, 1:10 dilution | 0 | 5 | MBS5411 |
| Day 5, 1:10 dilution | 2 | 3 | MBS7068 |
| Day 5, 1:5 dilution | | 5 | MBS7068 |
| Day 5, 1:10 dilution+2 hours | 3 | | MBS7068 |
| Day 6, 1:5 dilution | 0 | 4 | MBS7068 |
| Day 6, 1:10 dilution | 1 | 4 | MBS7068 |
| Day 8, 1:5 dilution | 5 | | MBS7068 |
| Day 8, 1:10 dilution | 5 | | MBS7068 |
| No pollinations made on Day 10 | | | |
| By Day 12, 1:5 pollen was too clumpy | | | |
| Day 12, 1:10 dilution | 5 | | PHP02 |

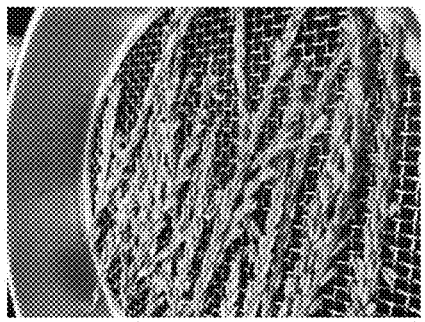
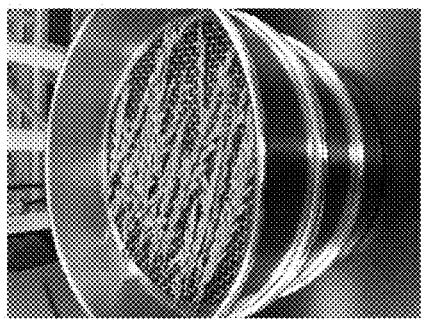
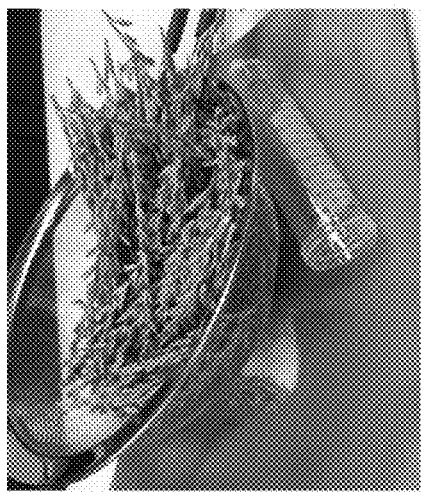
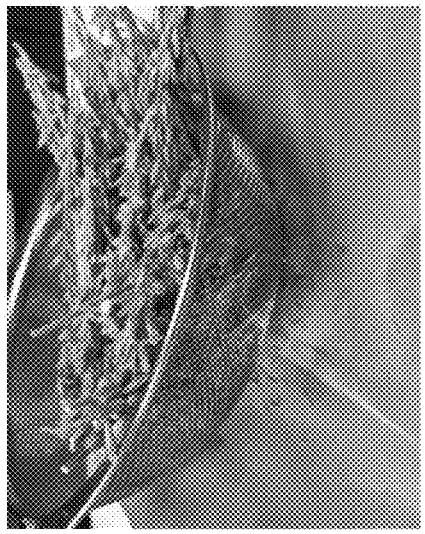
Figure 4

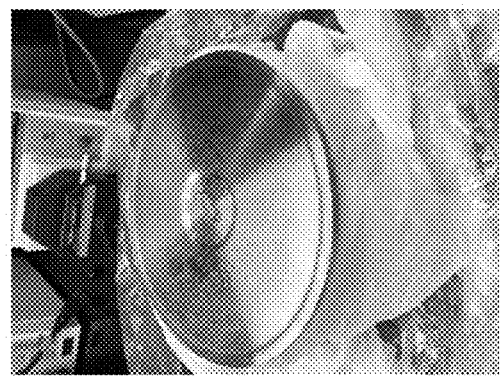
Figure 5

Figure 12
Pollinations made with 8-day-old pollen fraction that passed through the 0.18 mm sieve
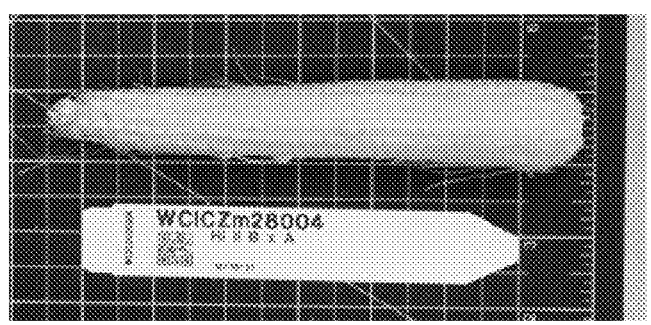
Pollination made with the 8-day-old pollen fraction that stayed on the 0.18 mm sieve
Pollinations made with fresh, diluted pollen

MAIZE POLLEN COMPOSITION FOR COLLECTING POLLEN AND STORING POLLEN

CROSS-REFERENCE TO RELATED APPLICATIONS

This application claims priority to U.S. Provisional Application No. 63/160,427 filed on Mar. 12, 2021, the contents of which are incorporated by reference in their entireties.

STATEMENT REGARDING FEDERALLY SPONSORED RESEARCH

This invention was made with government support under grant number 1917138 awarded by the National Science Foundation as 22-CRHF-0-6055 awarded by the USDA/NIFA. The government has certain rights in this invention.

BACKGROUND

Currently, maize breeding has systemic limitations. Pollen must be freshly collected and used immediately. However, maize silks (i.e., the female flower) and tassels (i.e., the male flower) are often not synchronized, which can result in lost breeding opportunities and potentially delay breeding by a full season or more. Even when silks and tassels are synchronized, successful pollination still depends upon favorable weather conditions. Temperature and rain can prevent the successful collection of pollen, which can cause breeders to miss the receptive window for pollination. Further, ideal silk receptivity is often in the early morning, while pollen shed may only occur after the dew evaporates off the tassels. This can result in a poor seed set for the breeding effort.

Maize pollen is commonly collected by covering the tassels with a paper pollination bag in the afternoon one day before pollination will be attempted. Pollination bags are taken down the following morning, and each bag is used to pollinate a single ear of maize. Once harvested, maize pollen is highly volatile and may be viable for anywhere from a few minutes to a few hours, depending on the pollen quality. Pollen collected using this standard method varies wildly in quality. In some cases, it is degraded and clumpy. Pollen may also be full of plant debris and insect parts. This high degree of variability in pollen quality can make the hand-pollination success rate low.

Further, the prevalence of low-quality pollen acts as a barrier for combining pollen from multiple plants, as a small amount of degraded pollen can spoil an entire batch. Individual pollen grains can burst under artificial conditions. As this occurs, neighboring grains are surrounded with cellular pollen contents and often react by bursting. This "cascade effect" can continue until the entire collection of pollen becomes unusable. This bursting effect can be seen under the microscope, and without a microscope one can see the once free-flowing pollen become clumpy and gummy. There is often a color change associated with this loss of quality.

In addition to the limitations it places on crop production, the inability to store large amounts of healthy, viable pollen is a major limitation for researchers who need pollen for laboratory experiments, including those aimed to develop crops with improved traits.

Accordingly, there remains a need in the art for maize pollen harvesting methods that produce high quality pollen with increased longevity.

SUMMARY

The present invention provides compositions comprising pollen and an inert powder, wherein the inert powder has a particle size that is between about 20% to about 200% the particle size of the pollen. In some embodiments, the compositions comprise a ratio of pollen to inert powder ranging from about 1:5 to about 1:10.

In a second aspect, the present invention provides methods of making the pollen compositions disclosed herein. The methods comprise (a) harvesting pollen from a plant; (b) straining the pollen through at least one sieve; (c) collecting the pollen that passes through the at least one sieve in a vessel; and (d) mixing the collected pollen with an inert powder, wherein the inert powder has a particle size that is between about 20% to about 200% the particle size of the pollen. In some embodiments, the methods further comprise (e) refrigerating the pollen in a sealed vessel, and optionally (f) straining the refrigerated pollen through at least one sieve prior to use.

In a third aspect, the present invention provides kits for making pollen compositions using the methods disclosed herein. The kits comprise (a) at least one sieve; and (b) an inert powder with a particle size that is between about 20% to about 200% the particle size of the pollen.

In a fourth aspect, the present invention provides methods of fertilizing a plant. The methods comprise applying the pollen compositions disclosed herein to the plant. In some embodiments, the plant is maize, hemp, wheat, sorghum, or cassava.

In a fifth aspect, the present invention provides methods of collecting pollen from a maize plant. The methods comprise (a) collecting maize tassels on the first day of pollen drop; (b) dividing the tassels into individual branches; (c) incubating the branches in a moist chamber overnight; (d) removing the branches from the moist chamber; and (e) collecting the pollen.

In a sixth aspect, the present invention provides vessels for collecting and sieving pollen from individual tassel branches or portions thereof. The vessels comprise an incubator tube and a receiving tube that are separated by a sieve. The vessel may further comprise a removal cap to seal the vessel and/or the incubator tube.

BRIEF DESCRIPTION OF THE DRAWINGS

The patent or application file contains at least one drawing executed in color. Copies of this patent or patent application publication with color drawing (s) will be provided by the Office upon request and payment of the necessary fee.

FIG. 2 is a table comparing the number of failed versus successful fertilizations made using the two pollen dilutions (i.e., 1:5 and 1:10) for several days following pollen harvest.

FIG. 4 shows photographs of the pollen shed produced by subjecting divided tassel branches to moist chamber maturation, as described in Example 3.

FIG. 5 shows photographs depicting the processing of further divided tassel branches for moist chamber maturation, as described in Example 4.

FIG. 12 shows examples of maize kernels harvested 11 days after pollination with fresh, diluted pollen (right), eight-day-old pollen that was retained on the number 80 mesh sieve (middle), or eight-day-old pollen that passed through the number 80 mesh sieve.

DETAILED DESCRIPTION

Figure 1:
FIG. 1 shows photographs of the ears of corn produced in the experiment described in Example 2. The first number above each ear indicates the day of the experiment, wherein day 1 is the day that the pollen was harvested. The second number indicates the dilution ratio, wherein "5" indicates a 1:5 ratio and "10" indicates a 1:10 ratio.

The present inventors have discovered a novel method for producing maize pollen with increased post-harvest longevity. In this method, debris and pollen clumps are removed from the pollen using one or more sieves. Then, the pollen is diluted with an inert powder that approximately matches the particle size of the pollen. The pollen compositions produced by this method remain stable under refrigeration for at least three days after the pollen is harvested, and the inventors have demonstrated that they can be used to fertilize a maize plant for at least eight days post-harvest. This represents a substantial improvement over standard practices, which require that the unstable pollen is used within a period ranging from minutes to hours from harvesting.

As used herein, the term "longevity" describes the length of time that pollen remains both viable and fertile. The term "viable" is used to describe pollen that is able to germinate and grow a pollen tube to at least a length twice the diameter of the pollen grain. In addition, pollen can be deemed viable by demonstration that its cells and cellular processes remain intact. The viability of pollen can be assessed in numerous ways including, but not limited to, assessment of pollen tube growth on artificial media or excised stigmas or styles, assessment of cellular intactness by vital staining of numerous sorts, absence of electrolyte (e.g., potassium) leakage, and impedance flow cytometry. Viable pollen can successfully germinate and commonly possesses the vigor necessary to promote fertilization and initiation of seed development. Non-viable pollen grains cannot successfully germinate. Not all viable pollen is also fertile pollen. In some cases, even when a pollen grain is viable and commences with pollen tube growth, it may lack the vigor necessary to reach the ovule and promote fertilization. The term "fertile" is used to describe pollen that is able to deliver sperm nuclei to the ovule and thereby effect double fertilization. In flowering plants, the term "double fertilization" refers to one sperm nucleus fusing with the polar nuclei to produce the endosperm tissues, and the other sperm nucleus fusing with the egg nucleus to produce the embryo.

The inventors' method offers several key advantages. First, by increasing the post-harvest longevity of the pollen, this method decouples the collection of pollen from the need for instant use on a receptive silk. This allows growers to wait to fertilize plants under good conditions (e.g., weather, silk receptivity, etc.), resulting in a more productive breeding effort. This also allows for large amounts of pollen to be stored for on-demand use, e.g., in research experiments. Further, because the pollen produced by this method can be transported without the need for extreme environmental temperature controls, it can be shared among distant collaborators.

In addition to increasing the longevity of the pollen, diluting the pollen provides increased flexibility with respect to the pollination strategy. Dilution allows the pollen from a single tassel to be used to fertilize many ears of maize as opposed to a single ear. Further, dilution allows the pollen to be applied with less skill and precision, including by mechanical means. Finally, the dilution step provides an opportunity for additional reagents to be applied to the pollen without any additional effort. Suitable additional reagents include, for example, reagents that prevent disease or insect predation, reagents used to select for certain transgenic pollen grains (e.g., within a heterozygous plant), and gene-editing reagents.

Finally, the methods of the present invention offer the advantage of simplicity. While other methods of long-term pollen storage have been described in the art, many such methods are quite complex and are not accessible to most research breeding programs, particularly those at more remote breeding stations. For example, U.S. Pat. No. 6,146,884 describes a method in which pollen is harvested into a series of chambers connected to a vacuum manifold and an air source. Pollen is repeatedly treated with pulses of two different reduced pressures by manipulating the machinery to alternatively vent and vacuum air. In one example, the pollen is treated with repeated cycles of 20 torr and 12 torr, with 105 seconds per cycle at the first pressure and 15 seconds per cycle at the second pressure. This method also requires the pollen to be oscillated at a very high frequency during this vacuum-drying treatment, between 20,000 Hz and 25,400 Hz, in order to mix the pollen continuously. U.S. Patent Publication No. 2020/0296954 provides another example of a complex method for producing maize pollen with increased longevity. In this application, pollen is harvested and pooled for field conditioning. Field conditioning of pollen was performed at 4° C. and 100% relative humidity by placing thin layers of pollen in hydrated petri plates. Field conditioning is done for several hours to improve pollen quality. After field conditioning, pollen can be further preserved by carefully removing moisture. The pollen is dried under controlled humidity and a partial vacuum, with a target of 60% moisture and 67-94 kPa. However, in cases where the goal is cryopreservation, the target moisture is 15-35%. In the most optimal method, the pollen is also treated with a partial vacuum and has a gas added to displace atmospheric oxygen. In contrast, the methods of the present invention are practical, inexpensive, and they require minimal equipment and training to implement.

Pollen Compositions:

The present invention provides compositions comprising pollen and an inert powder, wherein the inert powder has a particle size that is between about 20% to about 200% the particle size of the pollen. In some embodiments, the inert powder has a particle size that is between about 40% to about 160% the particle size of the pollen.

As used herein, the term "particle size" refers to the average diameter of a particle, or for particles that are non-spherical, the average diameter of a sphere that has the same volume as a given particle. By testing a variety of powders as pollen diluents, the inventors have discovered that using a powder that approximately matches the particle size of the pollen is key for extending the longevity of the pollen. Without wishing to be bound by theory, the inventors believe that the use of similarly sized particles (1) aides in mixing, reducing the damage to the delicate pollen grains, and (2) keeps the pollen evenly dispersed during storage, thereby preventing clumping. For example, in embodiments in which the pollen is from maize, which has a particle size of about 80-125 microns, the particle size of the inert powder may be between about 10-300 microns, 35-200 microns, 40-175 microns, or 50-200 microns. In embodiments in which the pollen is from hemp, which has the particle size of about 23-28 microns, the particle size of the inert powder may be between about 20-30 microns, 15-40 microns, or 10-50 microns. In embodiments in which the pollen is from wheat, which has the particle size of about 55-68 microns, the particle size of the inert powder may be between about 50-70 microns, 45-80 microns, or 35-90 microns. In embodiments in which the pollen is from sorghum, which has the particle size of about 37-45 microns on the longer axis, the particle size of the inert powder may be between about 35-50 microns, 30-55 microns, or 20-65 microns. In embodiments in which the pollen is from cassava, which has the particle size of about 90-148 microns, the particle size of the inert powder may be between about 85-150 microns, 80-160 microns, or 70-170 microns.

As used herein, the term "powder" refers to a bulk solid composed of many very fine particles that may flow freely when shaken or tilted. The term "inert powder" refers to a powder that is chemically inactive. In some embodiments, the inert powder used with the present invention is biodegradable. In some embodiments, the inert powder is "non-porous," meaning that air or liquid cannot pass through it. In some embodiments, the inert powder is "flowable," meaning it has the ability to flow. Preferably, the powder will facilitate mechanical flow and dispersion of the pollen during application. In some embodiments, the inert powder is "moisture resistant," meaning that it has the ability to resist absorbing moisture. In some embodiments, the inert powder is "a compound particle," meaning that it has more than a single layer and each layer may have different characteristics. An example of one such powder is a powder that absorbs moisture overcoated with a chemical that resists moisture. The term "relative humidity" (RH) refers to the amount of water vapor present in air and is expressed as a percentage of the amount needed for saturation at the same temperature. In Example 6, the inventors demonstrate that mixing pollen with polyether ether ketone (PEEK) powder maintains the relative humidity surrounding the pollen at a high level. This result suggests that by pre-equilibrating powders to high humidity (i.e., near 100% RH) other types of inert powders can be made suitable for long term pollen storage. Thus, the term "powder" is not limited in terms of internal relative humidity, such that a powder may have an internal relative humidity of 100%. In some embodiments, the inert powder is adjusted to high relative humidity, e.g., between about 75% to about 100% relative humidity.

In some embodiments, the inert powder is a plastic. In some embodiments, the inert powder comprises polyethylene microspheres or PEEK particles. For example, in embodiments in which the compositions comprises maize pollen, the inert powder may be Blue Polyethylene Microspheres (Cospheric LLC) or PEEK 450G-MP140 (i.e., a fine milled powder made from recycled PEEK 450G; manufactured by PolyClean Technologies, Inc.), which have particle sizes of approximately 106-125 microns and 50-105 microns, respectively. In some embodiments, the inert powder comprises biodegradable polymers (e.g., polyglycolic acid, polybutylene succinate, poly(p-dioxanone)). Other suitable polymers include, without limitation, nylon-like polyesters, polycarbonate, polypropylene, and the like.

In other embodiments, the inert powder is organic (i.e., derived from living matter). Suitable organic powders for use with the present invention may include, without limitation, lignin, gum rosin, silica, diatomaceous earth, ground plant products (e.g., corn silk, walnut shells), waxes (e.g., bee's, jojoba), and solidified plant oils. In some embodiments, the inert powder is a compound powder comprising more than one substance, e.g., wax-coated walnut shells. In some embodiments, the inert powder comprises agglomerated particles, such as a matrix of fine particles formulated with oxidized oil or wax and ground to an appropriate size. The inventors have demonstrated that two ratios of maize pollen to powder (i.e., 1:5 and 1:10) can be used to create pollen compositions that can be used to fertilize maize plants for an extended period post-harvest. Thus, in some embodiments, the composition comprises a ratio of pollen to inert powder ranging from about 1:5 to about 1:10. The inventors' results suggest that using a less diluted pollen composition may offer advantages in terms of potency, whereas using a more diluted pollen composition may offer advantages in terms of increased longevity (i.e., slower degradation), increased coverage, and ease of dispersal (e.g., by a tall tractor or drone). Thus, the optimal degree of dilution will vary depending on several factors, such as the availability of the pollen and the skill of the pollinator.

In some embodiments, the composition further comprises an additional reagent that protects the plant or improves a characteristic of the plant (e.g., oil content, kernel quality). In some embodiments, the additional reagent is selected from the group consisting of: a fungicide, an insecticide, a nematicide, a herbicide, a plant growth regulator, a microbial inoculant, a biostimulant, a nutrient, a fertilizer, a fertilizer enhancer, a dye, a colorant, a flowability agent, a polishing agent, a seed coating, double-stranded RNA, a mutagen, and a gene-editing reagent. Suitable gene-editing reagents include, without limitation, engineered nucleases, such as meganucleases, zinc finger nucleases (ZFN), transcription activator-like effector nucleases (TALENs), and nucleic-acid guided nucleases (e.g., Cas9); guide nucleic acids; template nucleic acids; and reagents that facilitate the delivery of nucleases and nucleic acids to a cell (e.g., recombinant viruses, nanoparticles). Genetic engineering is performed using several methods that are known in the art. Using these methods, new genetic material may be introduced into the cell directly (i.e., via injection, particle bombardment, nanoparticles, encapsulation, or electroporation) or delivered via another cell or a virus that is then fused with the cell. In some embodiments, genetic engineering involves altering the nuclear genome of the cell. When new genetic material is introduced to the nuclear genome, it can be inserted randomly or targeted to a specific location (e.g., via homologous recombination). In other embodiments, the engineered cell may harbor a vector comprising a target gene that is expressed independently of the nuclear genome. In some embodiments, the additional agent allows for selection of pollen with specific traits from a heterozygous individual (e.g., using a selectable marker and a particle sorting method). In one specific embodiment, the composition further comprises a fungicide that protects maize from corn smut. In some embodiments, the additional reagent is added in the form of a dry powder.

"Pollen" is a fine powdery substance consisting of microscopic grains or spores discharged from the male part of a flower or from a male cone. The pollen used with the present invention may be from any pollen-producing plant. Suitable plants include, without limitation, wheat, rice, maize, sorghum, soybean, alfalfa, hemp, beans, cassava, legumes, sugar beets, canola, and cotton. In some embodiments, the pollen is from maize, hemp, wheat, sorghum, or cassava. The compositions and methods of the present invention are particularly well-suited for use with (1) wind-pollinated plants (e.g., hemp, grasses) that have relatively unstable pollen, (2) self-pollinated plants (e.g., wheat) in which pollen is released in the glumes and does not travel well, and (3) plant species that normally require insects to move the pollen. The present invention also has utility for use with male sterile strategies and plastid-transformed crossing strategies.

In preferred embodiments, the compositions comprise pollen that is of high quality. For example, in some embodiments, the pollen is essentially free of debris. The term "debris" is used herein to refer to any non-pollen substance found in harvested pollen. Debris found in pollen commonly includes insects, insect parts, and plant parts (e.g., anthers). Removal of such debris should result in better quality, fungus-free pollen with enhanced and more predictable storability. As pollen degrades, it clumps together, precluding its use for simple dispersion methods and fertilization. Thus, in some embodiments, the pollen is free of large pollen clumps. As used herein, the term "stable" refers to pollen that has not begun to clump or degrade and remains capable of successful pollination. The quality of a sample of pollen can be assessed, for example, using a dissecting scope or by determining its ability to freely flow through a very fine sieve (e.g., a number 100 mesh sieve for maize pollen).

In preferred embodiments, the pollen in the composition is viable and fertile for an extended period of time post-harvest. Once harvested, maize pollen is highly volatile and may be viable for anywhere from a few minutes to a few hours, depending on the pollen quality. However, the inventors have discovered that mixing freshly harvested pollen with an inert powder extends the amount of time that it can be used to successfully fertilize a plant. Thus, within the compositions of the present invention, the pollen may be stable under refrigerated conditions for at least 12 hours, at least one day, at least two days, at least three days, at least four days, at least five days, at least six days, at least seven days, at least eight days, at least nine days, at least ten days, or for an even longer period after the pollen has been harvested. In some embodiments, the pollen is stable under refrigerated conditions for at least three to eight days. As used herein, the phrase "under refrigerated conditions" means maintained at a temperature of about 0.5° C. to about 8° C., preferably 4° C.

Methods of Making Pollen Compositions:

The present invention provides methods of making the pollen compositions disclosed herein. The methods comprise (a) harvesting pollen from a plant; (b) straining the pollen through at least one sieve; (c) collecting the pollen that passes through the at least one sieve in a vessel; and (d) mixing the collected pollen with an inert powder, wherein the inert powder has a particle size that is between about 20% to about 200% the particle size of the pollen.

The inventors have determined that refrigerating the pollen compositions produced by these methods increases their longevity. Thus, in some embodiments, the methods further comprise (e) refrigerating the pollen in a sealed vessel. Refrigeration may be performed in a standard refrigerator kept, for example, at a temperature of about 4° C. or below. For embodiments in which the pollen is harvested in the field, it may be advantageous to store the pollen in an insulated container or on ice prior to processing to prevent damage from excessive heat or desiccation.

As is described in Example 9, the inventors have discovered that straining a pollen composition that has been stored under refrigerated conditions for several days (e.g., 7-8 days) prior to use can further extend the amount of time that it can be used to successfully fertilize a plant. Thus, in some embodiments, the methods further comprise (f) straining the refrigerated pollen through at least one sieve prior to use.

The methods may also further comprise sorting the pollen prior to step (d). For example, the pollen may be sorted to select for pollen with a particular trait. This may be accomplished using a detectable marker that is associated with the trait of interest. Suitable detectable markers include, without limitation, colorimetric markers (e.g., RUBY, which converts the amino acid tyrosine to visually red betalain), luminescent markers, fluorescent markers, and enzymatic markers. Pollen containing the detectable marker can be sorted away from pollen that lacks the detectable marker using a fluorescent- or colorimetric-based sorting method (e.g., fluorescence-activated or colorimetric cell sorting) or it can be sorted away by hand (e.g., under a fluorescent microscope).

The inventors have determined that the longevity of the compositions is improved when the pollen is processed relatively soon after the pollen is collected (i.e., removed from the tassels). Thus, in some embodiments, the methods are performed within 16 hours of collecting the pollen.

In some embodiments, steps (b)-(d) of the methods are performed using equipment that has been devitalized between uses to remove any remaining pollen of the wrong type. In some embodiments, the equipment and work area are sterilized, i.e., to remove microorganisms such as bacteria, fungi, and their spores. The equipment may be devitalized and/or sterilized using any standard methods known in the art including, without limitation, washing with water, autoclaving, and treatment with a disinfectant (e.g., hydrogen peroxide, alcohol, chlorine, etc.). Sterile vessels (e.g., sterile tubes and flasks) may be purchased from commercial suppliers.

The sieve(s) used with the present methods may be any device that allows for the separation of unwanted elements (i.e., debris and pollen clumps) from the pollen. For example, the sieve(s) may comprise a woven screen, such as a mesh or net. The size of the holes in the sieve(s) should be selected based on the particle size of the pollen and the size of the unwanted elements to be removed. For example, the inventors have determined that a number 80 mesh sieve can be used to remove plant parts, insect parts, and large chunks of pollen, while allowing maize pollen grains to pass through. Thus, in some embodiments, the least one sieve used in part (b)and/or in step (f) comprises a number 80 mesh sieve.

In some embodiments, two or more sieves are used in part (b) of the methods. Sieves of different mesh sizes may be used to remove unwanted elements of different sizes. For example, for maize pollen, a number 20 mesh sieve (which comprises holes that are approximately 841 µm in size) may be used to remove large debris from the pollen, a number 80 mesh sieve (which comprises holes that are approximately 177 µm in size) may be used to remove relatively fine debris and large pollen clumps from the pollen, and a number 100 mesh sieve (which comprises holes that are approximately 149 µm in size) may be used to remove small pollen clumps from the pollen. Thus, in some embodiments, step (b) comprises (i) straining the pollen through a number 20 mesh sieve; (ii) straining the pollen through a number 80 mesh sieve; and (iii) straining the pollen through a number 100 mesh sieve. However, the size of the sieves used should be adjusted in accordance with the size of the pollen to be processed. For example, with hemp, a finer mesh sieve should be used in the final straining step. Those of skill in the art will understand that different mesh sizes will be appropriate for different pollen and plant types.

The term "vessel" is used to refer to an enclosure suitable for containing and storing pollen. A vessel can be of any size and material of construction. Suitable vessels for containing pollen include, without limitation, vials, beakers, flasks, jars, canisters, test tubes, microcentrifuge tubes, and the like. In certain preferred embodiments, the vessel used with the present invention is sterile. In embodiments in which the pollen is stored under refrigerated conditions, it is stored in a "sealed vessel," i.e., a vessel that is closed securely for example with a cap, such as a screw top cap, to prevent contamination or excessive moisture loss or gain.

The pollen used in step (a) of the present methods may be harvested by any suitable means known in the art. For example, pollen may be collected from freshly shedding flowers or male flower structures. In the case of maize, for example, pollen is collected from tassels (i.e., the male flowers of a maize plant), which may be attached to the plant or detached from the plant during collection. Additionally, the present inventors have discovered that tassels that are divided into individual branches or spikes (which may be further reduced in size to sections of individual spikes of approximately 6 centimeters or smaller) will produce higher quality pollen under controlled conditions. Singulation of tassel branches and further size reductions also allow for simpler automation of pollen release and collection. Further reduction to individual florets or anthers is also contemplated. The pollen may be collected from plants grown in any environment suitable for plant growth. Such environments include, but are not limited to, a field, a growth chamber, a greenhouse, a glasshouse, a shade house, a hoop house, a vertical farming facility, or a hydroponic facility. Alternatively, pollen may be collected directly from anthers by crushing or grinding the tassels and or isolated anthers, thereby releasing the pollen for collection. In addition, pollen may be collected from tassels cultured in vitro (Pareddy et al. (1989) Theor Appl Genet 77:521-526) or from tassels that have been removed from flowering structures at immature stages and matured off of the plant. The inventors have observed that a tassel can be removed from a maize plant several days prior to when it would naturally reach maturity and be allowed to mature in a temperature and humidity-controlled growth chamber. By modifying the temperature, the release of the pollen can be timed for ideal collection. Further, this harvesting method is easier than the standard method, which requires that pollen collection bags are applied to tassels that are often 6 or 7 feet from the ground and may be exposed to unfavorable weather conditions at the time of desired pollen maturity.

In step (c), the composition may be mixed using any method known in the art. However, it is advantageous that that mixing is gentle enough as to not disrupt the delicate pollen grains. Suitable methods of mixing include, for example, gentle shaking, rotation, air (e.g., from a cyclonic collector if vacuumed), and inversion.

In some embodiments, the methods of making the pollen compositions disclosed herein are automated. For example, the pollen may be harvested from anthers stored in a programable growth chamber, such as a Percival, in which light, humidity and temperature can be controlled. To automate the straining step, the anthers may be stored in a sieve placed on a commercial sieve shaker that is programmed to turn on at a predetermined time after the incubation of the anthers has begun. To automate the dilution step, the receiving pan below the sieve may be pre-loaded with inert powder. Finally, to automate the optional refrigeration step, the receiving pan may be kept under refrigerated conditions (e.g., via contact with an ice pack or a piezoelectric cooler).

The pollen produced by the disclosed methods is useful for fertilizing plants, as is discussed below. Additionally, the pollen produced by these methods may be used to elicit a specific biological effect. For example, maize pollen may be applied to oat or wheat to induce haploids.

Kits:

The present invention provides kits for making pollen compositions using the methods disclosed herein. The kits comprise (a) at least one sieve; and (b) an inert powder with a particle size that is between about 20% to about 200% the particle size of the pollen. In some embodiments, the kits comprise additional components, such as a vessel for collecting the pollen, a vessel to act as an incubation tube for the collected pollen, which may include a cap for sealing the vessel and an apparatus for manual pollination of plants.

Methods of Fertilizing Plants:

The present invention provides methods of fertilizing a plant. The methods comprise applying the pollen compositions disclosed herein to the plant. In some embodiments, the plant is maize, hemp, wheat, sorghum, or cassava.

To perform these methods, the pollen may be applied to the plant using any standard technique known in the art. Suitable techniques include, for example, shaking or blowing the pollen onto the female part of the plant. Various apparatus may be used to perform these techniques, including a simple vessel (e.g., a centrifuge tube with approximately 2-3 mm diameter holes in it for use with maize pollen), or a puffer (e.g., a commercial puffer applicator for diatomaceous earth). Other suitable apparatuses for small scale pollination include commercial saltshakers, small paint brushes, and dissection tools. Apparatus that are designed for automated or wide-spread applications (e.g., drones, aircraft, and modified tractors) may also be used. The application technique should be selected with both the plant species and the pollen dilution in mind. For example, when the pollen composition is more diluted, it may be advantageous to apply the pollen composition to the plant more liberally. When performing pollinations in the field, it may be advantageous to store the pollen composition in an insulated container prior to use to prevent damage from excessive heat or desiccation.

The inventors have demonstrated that the pollen compositions of the present invention are stable and can be used to successfully fertilize a plant for an extended period of time post-harvest. Thus, in some embodiments of the present methods, the composition is applied to the plant at least 12 hours, at least 1 day, at least two days, at least three days, at least four days, at least five days, at least six days, at least seven days, at least eight days, at least nine days, at least ten days, or for an even longer period longer after the pollen has been harvested. In some embodiments, the composition is applied to the plant up to 14 days after the pollen was harvested.

Methods of Collecting Pollen:

The present invention provides methods of collecting pollen from a maize plant. The methods comprise (a) collecting maize tassels on the first day of pollen drop; (b) dividing the tassels into individual branches; (c) incubating the branches in a moist chamber overnight; (d) removing the branches from the moist chamber; and (e) collecting the pollen. In some embodiments, the individual tassel branches are further divided in pieces that are about 6 cm to about 8 cm in length in step b. In some embodiments, the individual tassel branches are shaken of pollen, hand stripped of visible anthers, and/or washed with water prior to step c.

The inventors have determined that high humidity incubation extends the longevity of stored pollen. Thus, a "moist chamber" (i.e., a chamber in which the relative humidity can be controlled) is used in these methods. In one embodiment the relative humidity is maintained at over 75%, over 80%, over 85%, over 90%, over 95%, or up to 100% relative humidity.

Figure 6:
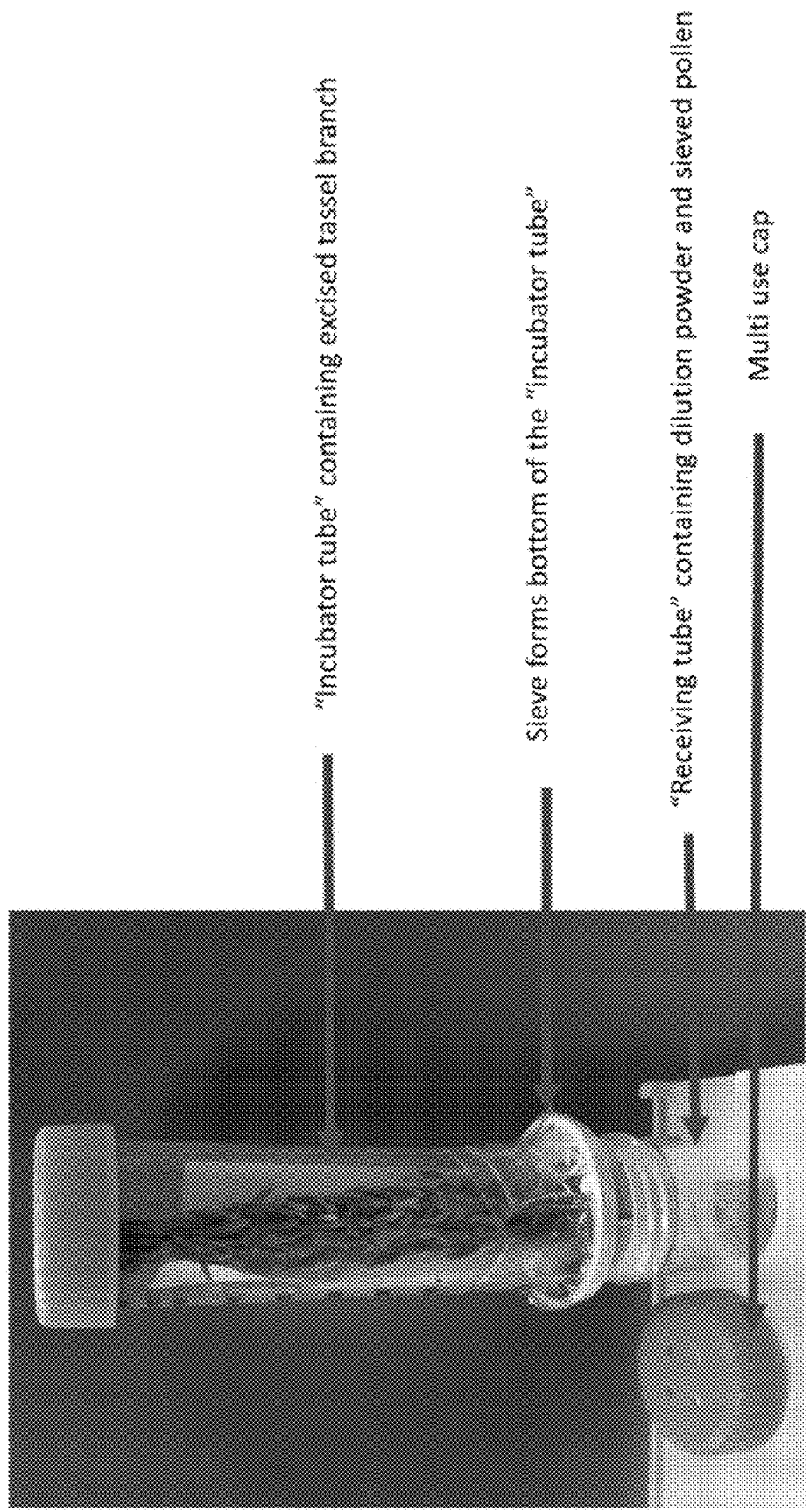
FIG. 6 shows a photograph of a vessel that was designed to incubate, collect, and sieve pollen from a single tassel branch into a storage tube. This vessel is described in Example 5.

Vessels for Collecting Pollen:

The present invention provides vessels for collecting and sieving pollen from individual tassel branches or portions thereof. The vessels comprise an incubator tube and a receiving tube that are separated by a sieve, as illustrated in FIG. 6 and described in Example 5.

The "incubator tube" is a cylinder capable of being capped. In some embodiments, the incubator tube is 50 milliliter centrifuge tube from which the bottom was been cut off. A rinsed tassel branch is added to the incubator tube and it is capped to maintain high moisture while the tassel is incubated at 23° C. to 28° C. to allow the anthers to quickly develop. The bottom of incubator tube is fused to a sieve. In some embodiments, the sieve has a mesh size ranging from about number 20 mesh to about number 80 mesh. These mesh size will vary depending on the type of pollen being collected.

The "receiving tube" a vessel capable of storing pollen. The bottom of the sieve is screwed into the top of the receiving tube, such that pollen released in the incubator tube can pass through the sieve into the receiving tube. In some embodiments, the receiving tube is 50 milliliter centrifuge tube. Advantageously, the receiving tube can be unscrewed from the sieve and tightly capped for storage of the collected pollen. In some embodiments, the receiving tube is preloaded with an inert powder that is to be mixed with the collected pollen.

When the tassel branch is ready to drop pollen, as is easily determined by anther extrusion, the cap is removed to allow the tube to be exposed to low humidity air and the pollen should begin to drop in 5 to 30 minutes. Vibration and or air movement can be used to aid in the process. The pollen drops through the sieve, which removes much of the plant debris, and into the receiving tube. The receiving tube can then be capped and stored under refrigeration until needed.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Example 1

The following example describes the initial experiments that were performed to assess the feasibility of pollen storage in 2019. The experiments were conducted in greenhouse and in field utilizing pollen and silks from the maize inbred line LH244.

Materials and Methods:

Pollen from LH244 tassels was greenhouse harvested and matured overnight in a laboratory in a moist chamber consisting of a large transparent plastic bag containing moistened paper towels. The pollen was then collected and purified using a series of sieves. The resulting purified pollen was mixed with several types of powder, including: Blue Polyethylene Microspheres (Cospheric LLC), diatomaceous earth, several sizes of commercial silica gels, and a commercial fine formulation of pearlite at a ratio of approximately 1:5 (pollen:powder). An unmixed pollen control was also included. The pollen-powder mixtures were placed in small glass containers and refrigerated at 4° C. These powders were applied to fresh silks of LH244 maize after 4 days of storage at 4° C. Two maize ears were pollinated for each treatment.

Results:

Most of the pollen-powder mixtures produced kernels. However, the greatest number of kernels were produced from the mixture containing Blue Polyethylene Microspheres (Cospheric LLC) and the control. When this experiment was repeated, the only treatment that produced a significant number of kernels was the mixture with Blue Polyethylene Microspheres (Cospheric LLC), as even the stored control produced no kernels. Surprisingly, mixing the pollen with these plastic spheres allowed for adequate dilution and storage life even with pollen of marginal quality. These results suggest that pollen quality is critical for successful storage and that the use of plastic powder should be optimized through additional studies.

Example 2

The following example describes an experiment that was performed in the field to determine whether a second plastic powder (i.e., PEEK) could be used in the disclosed pollen processing methods to increase the longevity of maize pollen.

Materials and Methods:

Pollen was collected from hybrids produced from a cross between a blue-pigmented kernel line and a yellow kernel line. Additional tested lines included inbred lines (i.e., PHP02, LH185) and proprietary licensed testers. Unless otherwise indicated, all pollen was harvested from appropriately aged tassels (i.e., tassels that had newly emerged anthers on that day, ideally a substantial number of new anthers) during good weather conditions (i.e., sunny, warm). The pollen was processed in the field. First, the pollen was sieved through one large mesh sieve (approximately number 20) and one small mesh sieve (approximately number 80) to remove debris, anthers, and clumped pollen. Then, the pollen was mixed with plastic powder in the ratio of 1:10 or 1:5 (pollen:powder) by volume. The pollen was stored in closed centrifuge tubes in a cooler in a cold room that is kept at approximately 4° C. The pollen was placed in the cooler within an hour of harvesting and processing the pollen, and the pollen was later used in a fertilization within an hour of removing the pollen from the cooler.

Five pollinations were made with each ratio batch each day for eight days post-harvest. On day one, several pollen application apparatuses were tested for feasibility, including a pollen puffer (referred to as Shawn's puffer in FIG. 2) and diatomaceous earth puffer (referred to as a Harris blaster in FIG. 2). However, the use of a saltshaker-like vessel with 2-3 mm holes in the cap proved to be most desirable for its ease of use and cleaning. Thus, a 50 milliliter centrifuge tube with holes in the cap was used for the remainder of the experiment. Leftover pollen that had been removed from refrigeration was discarded at the end of each day. Approximately three shakes of the tube were used to pollinate covered silks. The pollen-powder mixture was visible on the silks.

Additionally, to test the ability of heat to degrade the pollen compositions, a 1:10 ratio batch was capped and carried around outside for two hours before an additional three pollinations were made (referred to as "1:10 dilution+2 hours" in FIG. 2). None of these pollinations was successful.

Results:

To determine which pollinations were successful, the resulting corn ears were compared (FIG. 1 and FIG. 2), and fertilizations that produced corn ears with at least 10 kernels were deemed successful. The results demonstrate that the pollen-powder mixtures can be stored for 3-4 days prior to application. Additionally, while both dilutions worked well in this test, the results show that the 1:5 dilution of pollen yielded more kernels than the 1:10 dilution when the pollinations were performed using an amount of pollen corresponding to three shakes of the centrifuge tube. However, when the pollinations were performed using more generous shaking, the 1:10 dilution performed better. Further, while the 1:5 dilution became clumpy after seven days of storage, the 1:10 dilution remained shakeable (data not shown). Thus, while the 1:5 dilution may offer advantages in terms of potency, the 1:10 dilution may offer advantages in terms of shelf life.

Notably, pollen-powder mixtures were also made using tassel bags that had been hanging for two days, near the end of the tassels' lifespan. When these compositions were used in pollinations, they produced a low success rate (data not shown). These results suggest that the quality of the pollen used in the pollen-powder mixtures should be high enough that one would reasonably expect it to be used successfully in fertilizations at the time of mixing.

Figure 3:
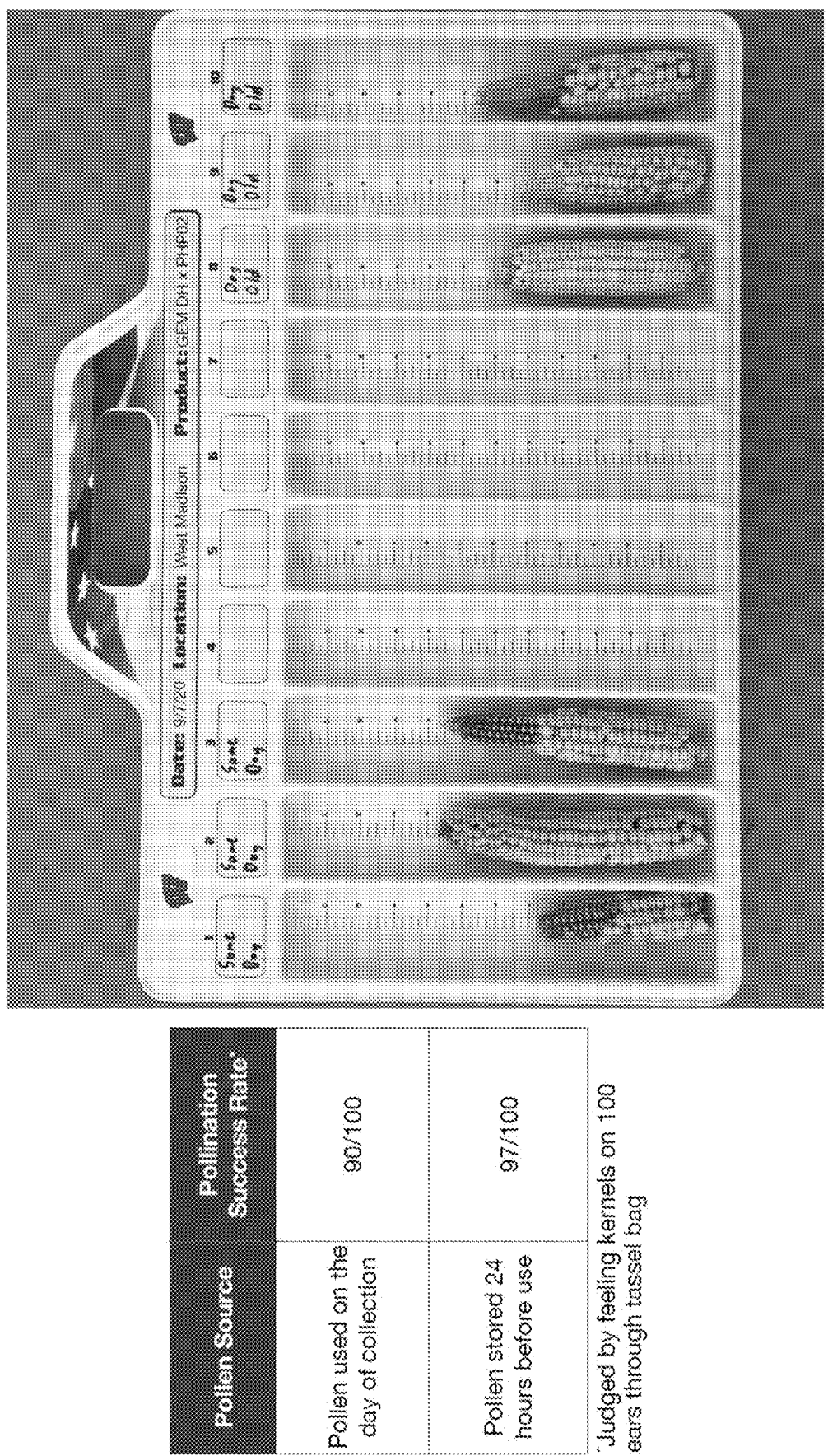
FIG. 3 shows a photograph of the corn ears produced in a second experiment described in Example 2.

The above experiment was repeated using the inbred line PHP02. The pollination success using pollen collected on the day of pollination was compared to the pollination success using pollen that had been stored for 24 hours prior to use (FIG. 3). The treated ears of corn were harvested later in the season and the success of the pollinations were visually assessed based on kernel fill. The pollinations with stored pollen were judged to be equivalent to those of the standard pollinations in the same row. Thus, storing pollen for a day prior to use did not diminish its potency.

Example 3

The inventors noticed that detached tassels that were not in contact with a nutrient solution performed as well as the tassels fed by the nutrient solution, indicating that incubation in a nutrient solution is not necessary if the internal moisture of the plant is adequate for continued development of the pollen in a moist chamber. This observation led the inventors to perform the experiments described in this example and Examples 4 and 5. In the following example, the inventors test the feasibility of automated collection and purification of pollen from the maize inbred line LH244.
Materials and Methods:

In January 2021, we conducted an experiment with maize tassels that were produced in a greenhouse. Divided spikes (branches) were prepared from a single LH244 maize tassel. The tassel was harvested on the first day of pollen drop in the PM after pollen shed (note: only the main spike was dropping pollen). The tassel was shaken of pollen, hand stripped of visible anthers, washed in a shower of RO water, and blotted dry. These were either placed on a clean mesh pan or on a rounded sieve and then placed in a moist chamber and allowed to develop overnight in the lab. The resulting pollen shed, shown in FIG. 4, occurred on Jan. 22, 2021 approximately 17 hours after harvest.
Results:

The pollen began to freely shed from the freshly developed anthers approximately 10 minutes after being removed from the moist chamber. The pollen was processed as described in Example 2, i.e., through a series of sieves using shaking. The moist chamber maturation step, the reduction in relative humidity, and the shaking of the sieves for harvest and purification could be easily automated. Pollen yield from the experiment was high, estimated at approximately 400 microliters.

Example 4

The following example describes a second experiment that was performed to test the feasibility of automated collection and purification of pollen from the maize inbred line LH244.
Materials and Methods:

As in Example 3, divided spikes (branches) were prepared from a single LH244 maize tassel that was produced in a greenhouse. However, in this experiment the branches were further reduced in size. Again, the tassel was harvested at first day of pollen drop in the PM after pollen shed (again, only the main spike was dropping pollen). The tassel was shaken of pollen, hand stripped of visible anthers, washed in a shower of RO water, and blotted dry. Then, each spike was excised and further divided into approximately 6 to 8 cm pieces. The pieces were placed on a clean mesh pan in a moist chamber and allowed to develop overnight in the lab, as depicted in FIG. 5.
Results:

The pollen began to freely shed from the freshly developed anthers approximately 30 minutes after being removed from the moist chamber. The pollen was purified as described in Example 2, i.e., through a series of sieves using shaking. Pollen yield from the experiment was high, measured at approximately 280 microliters.

Example 5

The following example describes a simple method to collect and mix pollen from a single tassel spike or section of a spike, and a vessel that can be used to accomplish this. This method allows for simplified selfing of a maize plant that may have male and female flowers emerging asynchronously. The vessel (shown in FIG. 6) comprises two parts, which allow for easy prelabeling of the pollen reservoir, powder addition, mixing, and storage after collection. The upper vessel (incubator tube) is a cylinder capable of being capped that is fused to a mesh at the bottom (approximately number 20 to number 80 mesh). A rinsed tassel branch is added to this incubator tube and it is capped to maintain high moisture while it is incubated at 23° C. to 28° C. to allow the anthers to quickly develop. The incubator tube is built in such a way that it nests in a standard 50 milliliter sterile disposable centrifuge tube that is also threaded to receive a tightly fitting cap. This receiving tube can be preloaded with an appropriate amount of dilution powder and can also be pre-labeled to allow for errorless collection, storage, and eventual pollination. When the tassel branch is ready to drop pollen, as is easily determined by anther extrusion, the cap is removed to allow the tube to be exposed to low humidity and the pollen should begin to drop within 5 to 30 minutes. Vibration and or air movement can be used to aid in the process. The pollen drops through the sieved bottom of the incubator tube, which removes much of the plant debris, and into the pre-labeled receiving tube containing the dilution powder. The receiving tube can then be capped, mixed gently, and stored under refrigeration until the pollen-powder mixture is needed.

Example 6

Figure 7:
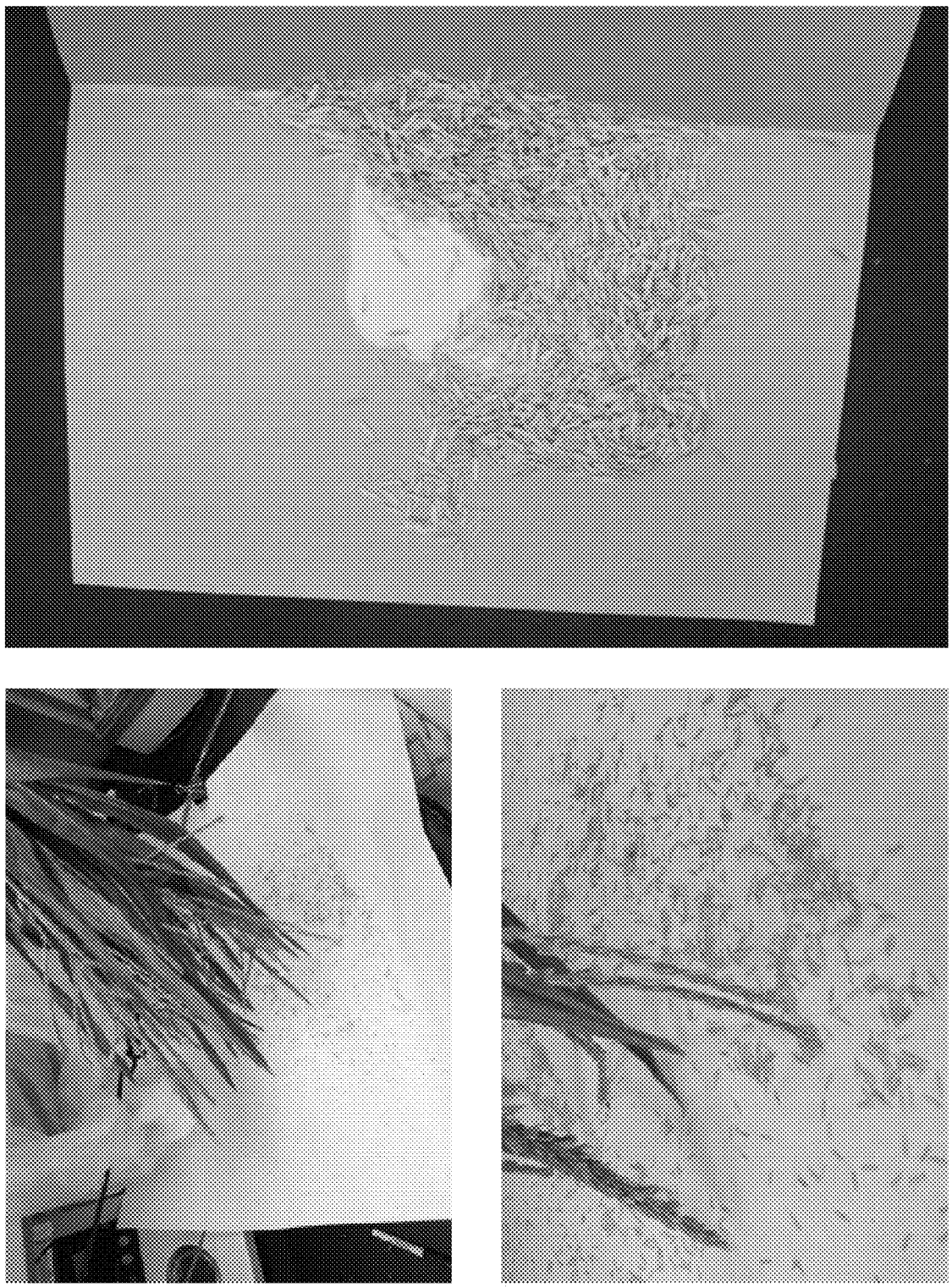
FIG. 7 shows photographs depicting the collection of LH244 maize pollen in the experiment described in Example 6.
Figure 8:
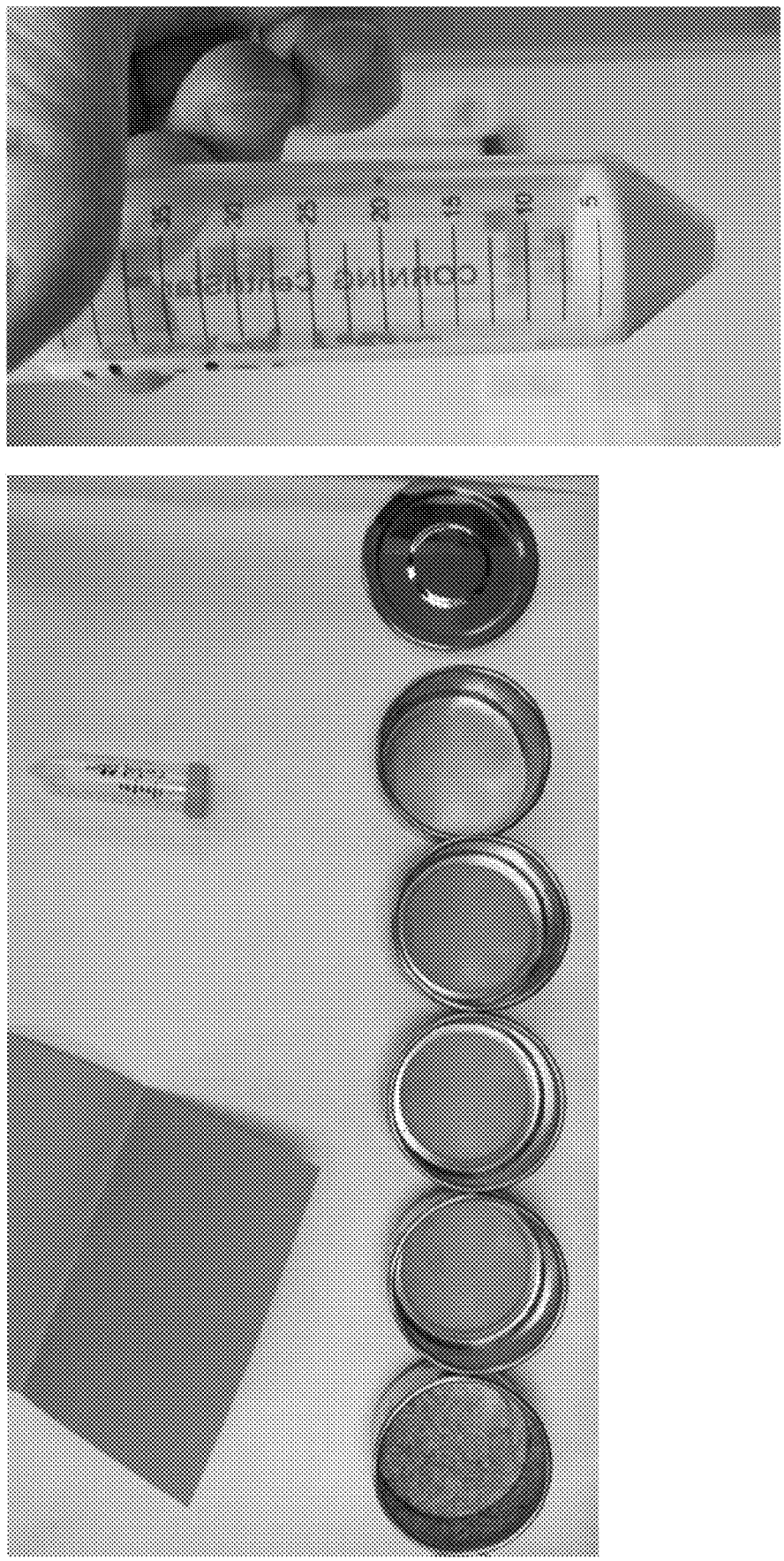
FIG. 8 shows photographs depicting the dilution of the pollen collected in FIG. 7.

The following example describes an experiment that was used to test the effect of storage humidity on the storage life of the pollen-powder mixture.
Materials and Methods:

As shown in FIG. 7, maize tassels of genotype LH244 were harvested and were then exposed to dryer lab air for 5 to 10 minutes until pollen began to drop. Then, the tassels were shaken over a clean piece of butcher paper and the released pollen was quickly poured onto clean blue card paper to determine its quality. 5.0 milliliters of purified pollen (or 0.4 milliliters per tassel) was measured from the AM pollen shed. The pollen was then collected as shown in FIG. 8. The pollen was purified using a sieve and was then measured in a sterile tube.

The fresh, sieved pollen was mixed at 1:10 with PEEK powder on Jan. 21, 2021. A sample of this mixture was placed in a sealed tube and was immediately stored under refrigerated conditions (i.e., at 4° C.) to serve as the internal control for this experiment. This sample is referred to hereafter as the refrigerated pollen-powder mixture. Additional samples were spread into a thin layer (approximately 2 millimeters thick) in one sterile petri dish for each humidity tested. These petri dishes were equilibrated at the following (approximate) relative humidity (RH): 0% RH, 23% RH, 58% RH, 75% RH, and 100% RH. Saturated salts were used to create humidity at 4° C., a method that is widely used in chemistry. 0% RH was created using the standard lab desiccant Drierite. 23% RH was created by using a saturated solution of potassium acetate. 58% RH was created by using a saturated solution of magnesium nitrate. 75% RH was created by using a saturated solution of sodium chloride. 100% RH was created using distilled water. All equilibration was conducted in tightly closed plastic boxes, with the thin layer of pollen-powder mixture exposed within the controlled environments. Additionally, pollinations were conducted immediately after pollen was mixed (i.e., at a 1:10 ratio of pollen to PEEK powder) to serve as a pollen quality control. A standard pollination was also conducted with pollen straight from a tassel to assess the quality of the silks at the time of the experiment. All humidity-equilibrated pollen-powder mixtures were used for pollination on Jan. 22, 2021 to test the effect of 24 hours of exposure to the controlled humidity environment. The refrigerated pollen-powder mixture was also used for pollination at 24 hours. An exposure control was also conducted on Jan. 22, 2021, which involved exposing a silk for the time it takes to achieve a standard pollination (about 5 to 10 seconds). This control is designed to demonstrate that the area and environment are well controlled for extraneous pollen.

Figure 9:
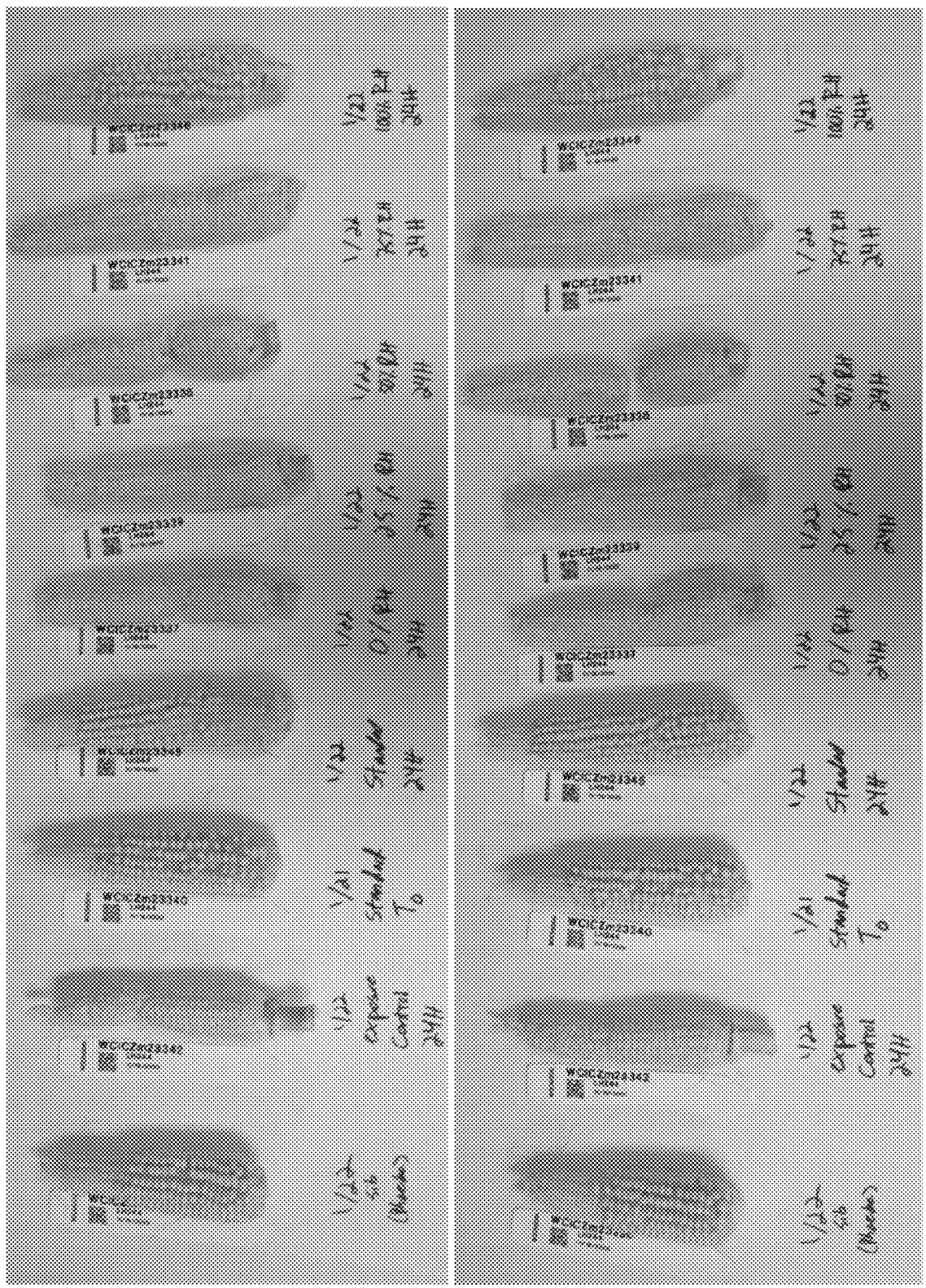
FIG. 9 shows photographs depicting the results of the pollination experiment described in Example 6. Each maize ear was pollinated with 0.1 ml of pollen-PEEK mixture. Photographs were taken 12 days after pollination. In the bottom photo, the ears were rotated 180 degrees from their position in the top photo. The exposure control, which was pollinated with 0.1 ml PEEK powder without pollen, has no kernels. The standard hand pollination control (Sib) is only ⅔ filled. Pollinations with the unequilibrated pollen-PEEK mixture produced similar results when the mixture was used directly and when it was used after 24 hours storage. All ears treated with pollen-PEEK mixtures that were equilibrated at humidity values of less than 75% RH had no kernels, whereas those treated with pollen-PEEK mixtures equilibrated at 100% humidity were substantially similar to the unequilibrated pollen-PEEK control.

Results:

Results were evaluated on Feb. 3, 2021, 12 days post pollination (FIG. 9). The control pollinations performed immediately after the pollen-PEEK mixture was prepared yielded high kernel counts, which demonstrates that the mixture was active prior to storage. We noted a significant difference in the pollinations that were conducted after 24 hours in storage. The refrigerated pollen-PEEK mixture performed well with high numbers of kernels developing, similar to the standard pollination from a tassel. No kernels were produced from the pollen-powder mixture that was subjected to 0% RH, 23% RH or 58% RH equilibrations. Only a few kernels were produced from the pollen-powder mixture subjected to the 75% RH equilibration. The pollen-powder mixture subjected to the 100% RH equilibration, the refrigerated pollen-powder mixture, and standard pollination from a tassel all produced high kernel numbers. The exposure control produced no kernels, validating the experimental results. These results demonstrate that the PEEK powder maintains the relative humidity surrounding the pollen at high RH in the microenvironment, likely near 100% RH. This suggests that by pre-equilibrating powders to high humidity, other types of inert powders can be made suitable for long term pollen storage. Thus, powders that offer additional benefits (e.g., powders comprising pollen-modifying agents) could be utilized. When this storage experiment was conducted with pollen diluted 1:5 with PEEK, identical results were observed (data not shown).

Example 7

The following example provides pollen calculations.

An average maize pollen grain has a diameter of 80-125 μm (enveurope.springeropen.com/articles/10.1186/s12302-014-0024-3). The average between these extremes is 103 μm.

The typical yield of pollen from 8-10 cut, lab-stored tassels is 5 mL per day. We can get 3-5 mL per day for 3 days.

103 μm is equivalent to $103 \times 10^{-5}$ cm

The volume of one average grain of pollen is:

$$\tfrac{4}{3} \times \pi \times (103 \times 10^{-9}\ \text{cm})^3 = 4.58 \times 10^{-9}\ \text{cm}^3 \text{ per grain}$$

In 5 mL of pollen, assuming that 100% of space is taken up by pollen, there would be approximately:

$$\frac{5\ \text{mL}}{4.58 \times 10^{-9}} \text{ grains of pollen} = 1{,}090{,}000{,}000 \text{ grains of pollen}$$

However, pollen is a sphere and spheres have a limited packing density due to their shape. The maximum packing density of randomly distributed spheres is 0.64 (JAEGER, H. M., & NAGEL, S. R. (1992). *Physics of the Granular State. Science* 255(5051), 1523-1531).

If we correct our estimate of pollen grains in 5 mL using the packing density, we get:

$$1{,}090{,}000{,}000 \text{ grains of pollen} \times 0.64 = 698{,}000{,}000 \text{ grains of pollen}$$

Per 1 mL, that is 140,000,000 grains of pollen.

If we dilute pollen 1:5 (pollen:powder), 1/6 of the total volume is pollen. Thus, in 1 mL of 1:5 diluted pollen, there are:

$$\tfrac{1}{6} \times 140{,}000{,}000 = 23{,}300{,}000 \text{ grains of pollen}$$

That means that in our pollinations with 100 μL of diluted pollen powder, we are adding approximately:

$$100\ \mu\text{L} \times \frac{1\ \text{mL}}{1000\ \mu\text{L}} \times 23{,}300{,}000 = 2{,}330{,}000 \text{ grains of pollen}$$

Assuming that we want to pollinate an inbred variety that typically produces 200-400 kernels (300 average) by hand-crossing, and that one pollen grain is needed per silk, we can perform a successful pollination with the following percentage of remaining viable pollen in a 100 uL aliquot:

$$\frac{300\ \text{kernels}}{2{,}330{,}000\ \text{grains per 100}\ \mu\text{L}} \times 100 - 0.0129\%$$

Thus, 99.99% of the pollen can die and there would still be enough viable grains to perform a single pollination with these assumptions. Likewise, the minimum amount of diluted pollen necessary to pollinate a single ear is:

$$\frac{300\ \text{kernels}}{23{,}300{,}000\ \text{grains per}\ \mu\text{L}} = 0.000129\ \text{mL} = 0.129\ \mu\text{L}$$

This also means that our typical volume of 100 μL of 1:5 diluted pollen could pollinate approximately 775 ears of maize.

$$\frac{100\ \mu\text{L aliquot}}{0.129\ \mu\text{L per ear}} = 775\ \text{ears}$$

Example 8

In the previous examples, the ability of the disclosed pollen processing method to increase pollen longevity was tested in greenhouse environments and in small, controlled field experiments (see Example 2). Successful application of this method to an entire field would suggest that it could replace traditional hand crosses performed via pollen splitting, i.e., placing pollen collected from a single tassel bag directly onto several ears. Therefore, in the following example, the feasibility of applying this method to an entire field was tested. Specifically, the inventors sought to: (1) determine whether the method could be applied to a variety of inbred maize lines, (2) compare the efficiency of the method to that of traditional pollen splitting, and (3) empirically evaluate the number of maize kernels that can be obtained on a field level using the method.

Materials and Methods

The pollen processing method was applied to a whole field in a trial performed in the summer of 2021 in Madison, Wis. For this field experiment, the pollen was diluted 1:5 in PEEK powder. Fresh pollen was collected from tassel bags in the morning at the peak of pollen shed and sifted twice to remove anthers and debris. PEEK powder was added to the pollen, and the mixture was turned over to gently homogenize it. All pollen mixing was performed in a four-ounce collection cup and all steps, including pollen collection, mixing, and sifting, were conducted on ice to avoid pollen desiccation from the heat. Following mixing, the homogenized pollen-PEEK mixture was directly used to pollinate fresh silks. Excess pollen-PEEK mixture was stored for 24 hours and was used to pollinate fresh silks the following day. The pollen-PEEK mixture was transferred to fresh silks via a glass vessel (saltshaker) with 1/16 inch holes. The pollen-PEEK mixture was used for six independent experiments in one field, allowing for a systematic analysis across 12 different inbred pollen parents.

Results

Pollen from different plant lines can vary significantly in characteristics such as stickiness, size, shape. Thus, the first goal of the present experiment was to test the utility of the pollen processing method on various inbred parents. To do so, the method was applied to over 12 different inbred pollen parents during the summer of 2021. Successful pollen storability was achieved across all inbred lines. Therefore, the method does not appear to be inbred-dependent, suggesting that it can be used to process the pollen of diverse maize inbred lines.

The second goal of this experiment was to test if the use of the stored pollen-powder mixture could replace the use of traditional pollen splitting for pollination of an entire field. We observed a substantial increase in pollination efficiency using the pollen-PEEK mixture relative to pollen splitting. This gain in efficiency was a result of the decreased number of tassel bags assemblies that were required to perform the pollinations using the pollen-PEEK mixture as compared to using pollen splitting. This gain in efficiency is demonstrated in Table 1, which shows that one tassel bag of collected pollen can pollinate approximately three independent ears using the traditional method, whereas one tassel bag of collected pollen can pollinate approximately 13-45 when it is diluted 1:5 with PEEK.

In Example 7, the hypothetical efficiency in terms of available pollen grains and pollinated kernels was described. This number was empirically evaluated during the summer of 2021 as part of the present experiment. The average efficiencies over two replications for three different inbred pollen parents are summarized in Table 1. The relative efficiency is based on an application of three shakes of pollen-PEEK per silk from the saltshaker. The quantity of the pollen-PEEK mixture released from three shakes of the saltshaker was measured 20 times using a scale. This quantification revealed that an average of 0.047 g (±0.003 g) of the mixture was released per pollinated ear (data not shown).

Using an estimated amount of 0.05 g of pollen-PEEK mixture per ear, we observed a 4.62- to 15.51-fold increase in efficiency using the pollen-PEEK mixture relative to pollen splitting. This relative efficiency was estimated by dividing the number of pollinations that were made using the pollen-PEEK mixture by the estimated number of hand pollinations that would have been made (assuming three pollinations per tassel bag). The relative efficiency was estimated for the three inbred parents PHJ89, PHK76, and PH41E. The variation in the relative efficiency between inbred parents may be the result of a "nick" (i.e., timing difference) between pollen shed and silk receptivity. Alternatively, this variation could be the result of daily differences in humidity and temperature, which affect the quantity of pollen released from the tassel and hence the number of pollinations that can be made per tassel bag.

Together, these results demonstrate that pollinating an entire field with the pollen-PEEK mixture is possible and is significantly more efficient than making hand crosses using pollen splitting. We note that the benefits of using stored pollen and/or PEEK-diluted pollen are even greater during times of environmental stress that reduce the quantity of available pollen.

Figure 10:
FIG. 10 shows examples of maize kernels harvested during the 2021 field season from ears that were pollinated with a 1:5 pollen-PEEK dilution mixture, as described in Example 8. Ears that were pollinated with pollen-PEEK mixture that was stored for 24 hours are shown on the left and ears that were pollinated with pollen-PEEK mixture that was stored for 48 hours are shown on the right. The individual ears shown in the bottom photos were treated with fresh (non-stored pollen. The fresh (non-stored) controls with the control for 24 hours storage in the left foreground and the control for 48 hours of storage in the right foreground. For these controls the pollen was collected and used on the same day (either one or two days after collection of the pollen used in the top photographs) using standard hand pollination without any storage.

The third objective of this experiment was to empirically identify how many maize kernels could be obtained using the pollen-PEEK mixture. This was assessed across six different experiments performed on various commercial and publicly available inbred maize lines. The six experiments ranged in size from 88 to 446 plots with six pollinations made per plot. As is shown in Table 2, 700 to 1400 maize kernels were successfully harvested per experiment using the pollen-PEEK mixture. These results suggest that the use of the pollen-PEEK mixture is a suitable substitute for pollen splitting for the pollination of entire fields. Examples of maize ears pollinated using the pollen-PEEK mixtures are shown in FIG. 10. We observed no difference in the relative number of successful pollinations on a field level compared to what would have been observed if pollinations were done by hand (qualitative observation).

TABLE 1

Relative efficiency of using the pollen-PEEK mixture compared to traditional pollen splitting amongst three usefulness of expired proprietary (Ex-PVP) inbred lines

| Inbred line | Number of tassel bags | Pollen. quantity (ml) | Pollen per bag | Dilution quantity (ml) | No. of possible pollinations (0.05 g/ear) | Est. hand pollinations | Relative efficiency (RE) | Std. error for RE |
|---|---|---|---|---|---|---|---|---|
| PHJ89 | 22 | 6 | 0.28 | 35 | 700 | 66 | 10.61 | 2.50 |
| PHK76 | 33 | 3.5 | 0.11 | 22.5 | 450 | 97.5 | 4.62 | 0.87 |
| PH41E | 22 | 9 | 0.40 | 50 | 1000 | 66 | 15.15 | 3.19 |

TABLE 2

Harvested kernels from maize treated with the pollen-PEEK mixture, measured in 12 different inbred parents and six different experiments

| Experiment Name | Average kernels harvested per plot | Number of plots pollinated | Total number of kernels harvested |
|---|---|---|---|
| Pollen storage across 8 Ex-PVP testers | 837 | 446 | 373444 |
| Pollen storage with LH244 | 900 | 146 | 131357 |
| Commercial inbred 1 | 918 | 145 | 133066 |
| Commercial inbred 2 | 703 | 340 | 238865 |
| Commercial inbred 3 | 612 | 341 | 208804 |
| Pollen storage across PHP02 and PH24E | 1406 | 88 | 123707 |

As with the relative efficiency, the differences in the quantity of maize kernels harvested among the inbred lines appear to be due to environmental factors such as temperature and humidity and not due to differences in the inbred pollen parents. The effect of humidity on pollen viability is supported by the fact that inbred pollen parents that shed pollen during times of high humidity released less pollen and that this pollen produced fewer maize kernels.

Finally, we note that a major advantage of utilizing a pollen-powder mixture to pollinate a field is that it requires less labor than pollen splitting. With a pollen-powder mixture, only three to four workers are needed. One worker makes the dilution, one worker places the pollen onto the silks, and two to three workers cover the silks with tassel bags. Many more workers (i.e., approximately 10-12) are needed to accomplish the same number of pollinations via pollen splitting.

Example 9

The following example describes an experiment performed to test a method for enriching a stored sample of diluted pollen after a period of storage. This experiment was conducted in a greenhouse using donor plants of the transformable hybrid Hi II A×B.

Materials and Methods:

Hi II A×B tassels were harvested one day prior to pollen harvest from the greenhouse, rinsed with ddH$_2$O, patted dry with paper towels, and covered with pollination bags. Cut tassels were placed in a 1 L tri-pour beaker with 500 mL of prepared 1×FloraLife solution, and were then incubated on a lab bench at approximately 22° C. Pollen was harvested in the morning and poured through a number 100 mesh screen. The pollen was then poured into a microfuge tube to measure the approximate volume, and then 5 times the volume of pollen of PEEK MP140 (PolyClean Technologies, Inc.) was measured and carefully poured into a 15 mL centrifuge tube. The pollen was then added to the PEEK powder and the two were mixed by gently inverting the tube. The diluted pollen was then stored at 4° C.

After seven days of storage, the pollen-PEEK mixture was poured through a sieve with a gap size of 0.18 mm (i.e., a number 80 mesh screen) and collected on construction paper. Both fractions, i.e., the fraction that passed through the sieve and the fraction that was retained on top of the sieve, were collected, transferred into centrifuge tubes, and stored overnight. Pollinations were attempted the next day (i.e., after eight days of storage). Pollinations were performed quickly to minimize exposure of the pollen-PEEK mixture to the greenhouse and to minimize exposure of silks to other sources of pollen. Shoot bags from ears of Hi II A×B were removed one at a time and the diluted pollen was tapped carefully from the centrifuge tube onto the silks. Since some degree of pollen degradation was expected, an excessive amount of diluted pollen was used: approximately 0.5 mL of diluted pollen was used for one to two pollinations. After the diluted pollen was added to the silks, a pollination bag was immediately placed over the ear. Fresh pollen that was harvested that same day was diluted in a similar manner to the stored pollen and used as a positive control.

Figure 11:
FIG. 11 shows the two fractions of the pollen-PEEK mixture obtained from re-sieving with a number 80 mesh sieve following seven days of storage. The fraction on the left was retained on top of the number 80 mesh sieve and had the clumped appearance of pollen which had been stored too long. The fraction on the right passed through the number 80 mesh sieve and more closely resembled fresh, diluted pollen.

Results:

Re-sieving the stored pollen through a number 80 mesh sieve after seven days produced two approximately equal volume fractions. The fraction that passed through the sieve resembled fresh, diluted pollen, while the fraction that was retained on top of the sieve consisted primarily of large clumps (FIG. 11). The pollinations made with fresh diluted pollen performed well, as expected, and produced relatively full ears, whereas the pollinations made with pollen that was stored for eight days prior to use produced results that varied depending upon the fraction that was used. The stored pollen that was retained on top of the number 80 mesh sieve produced an ear with only a few sparse kernels. In contrast, the stored pollen that passed through the number 80 mesh sieve produced ears with many more kernels than the retained fraction (FIG. 12). These results suggest that pollen can be enriched for quality during storage via re-sieving, and that issues with poor ear fill in ears pollinated with diluted pollen may be due to a high percentage of nonviable, clumped pollen.

What is claimed:

1. A composition for collecting pollen and storing pollen comprising pollen and an inert powder, wherein the pollen is from maize, wherein the inert powder comprises polyether ether ketone particles, and wherein the particle size of the polyether ether ketone is between about 50 microns to about 200 micron.

2. The composition of claim 1, wherein the composition comprises a ratio of pollen to inert powder ranging from about 1:5 to about 1:10.

3. The composition of claim 1, wherein the composition further comprises an additional reagent selected from the group consisting of: a fungicide, an insecticide, a nematicide, a herbicide, a plant growth regulator, a microbial inoculant, a biostimulant, a nutrient, a fertilizer, a fertilizer enhancer, a dye, a colorant, a flowability agent, a polishing agent, a seed coating, double-stranded RNA, a mutagen, and a gene-editing reagent.

4. The composition of claim 1, wherein the pollen is stable under refrigerated conditions for three to eight days.

* * * * *